(12) United States Patent
Berthusen

(10) Patent No.: US 8,096,992 B2
(45) Date of Patent: Jan. 17, 2012

(54) REDUCED PROFILE ORTHOPAEDIC REAMER

(75) Inventor: Andy Berthusen, Leesburg, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 733 days.

(21) Appl. No.: 11/387,533

(22) Filed: Mar. 23, 2006

(65) Prior Publication Data

US 2007/0225723 A1    Sep. 27, 2007

(51) Int. Cl.
*A61B 17/58* (2006.01)
(52) U.S. Cl. ............................. 606/81; 606/80
(58) Field of Classification Search ............ 606/79, 606/80, 81, 86 R, 171, 178, 179; 623/22.21, 623/22.22, 22.23, 22.24, 22.25, 22.26, 22.27, 623/22.28, 22.29, 22.3, 22.31, 22.32, 22.33, 623/22.34, 22.35, 22.36, 22.37, 22.38, 22.39, 623/22.4, 22.41, 22.42, 22.43, 22.44, 22.45, 623/22.46, 23.11, 23.12, 23.13
See application file for complete search history.

(56) References Cited

U.S. PATENT DOCUMENTS

| 4,116,200 | A | * | 9/1978 | Braun et al. | 606/81 |
|---|---|---|---|---|---|
| 4,662,891 | A | * | 5/1987 | Noiles | 623/22.31 |
| 5,203,653 | A | * | 4/1993 | Kudla | 408/207 |
| 5,282,804 | A | | 2/1994 | Salyer | 606/86 |
| 5,658,290 | A | | 8/1997 | Lechot | 606/80 |
| 6,129,732 | A | * | 10/2000 | Lechot | 606/80 |
| 6,221,076 | B1 | * | 4/2001 | Albrektsson et al. | 606/80 |
| 6,245,074 | B1 | * | 6/2001 | Allard et al. | 606/80 |
| 6,250,858 | B1 | | 6/2001 | Salyer | 408/239 |
| 6,283,972 | B1 | | 9/2001 | Riley | 606/81 |
| 6,409,732 | B1 | | 6/2002 | Salyer | 606/91 |
| 6,730,094 | B2 | * | 5/2004 | Salyer et al. | 606/80 |
| 7,220,264 | B1 | * | 5/2007 | Hershberger | 606/81 |
| 7,479,144 | B2 | * | 1/2009 | Myers | 606/80 |
| 7,588,572 | B2 | * | 9/2009 | White et al. | 606/80 |
| 7,608,076 | B2 | * | 10/2009 | Ezzedine | 606/81 |
| 7,611,515 | B2 | * | 11/2009 | Wolford et al. | 606/80 |
| 2003/0078587 | A1 | | 4/2003 | Lechot et al. | 606/81 |
| 2003/0212401 | A1 | * | 11/2003 | Nordman | 606/80 |
| 2003/0220647 | A1 | * | 11/2003 | McCallum et al. | 606/81 |
| 2003/0229356 | A1 | | 12/2003 | Dye | 606/99 |
| 2004/0097947 | A1 | | 5/2004 | Wolford et al. | 606/80 |
| 2004/0167528 | A1 | | 8/2004 | Schantz | 606/81 |
| 2006/0264958 | A1 | * | 11/2006 | Ezzedine | 606/81 |

FOREIGN PATENT DOCUMENTS

WO    WO 03/086208    10/2003
WO    WO 2004/024007    3/2004

* cited by examiner

*Primary Examiner* — Eduardo C Robert
*Assistant Examiner* — Jan Christopher Merene
(74) *Attorney, Agent, or Firm* — Taylor IP, P.C.

(57) ABSTRACT

An orthopaedic reamer, which includes a reamer with a partially hemispherical shell which has a base including three circumferential base segments. The shell has three cutouts each extending to the base. Each of the three circumferential base segments are separated from another of the three circumferential base segments by one of the three cutouts. A driver attachment is directly connected to the three circumferential base segments.

3 Claims, 3 Drawing Sheets

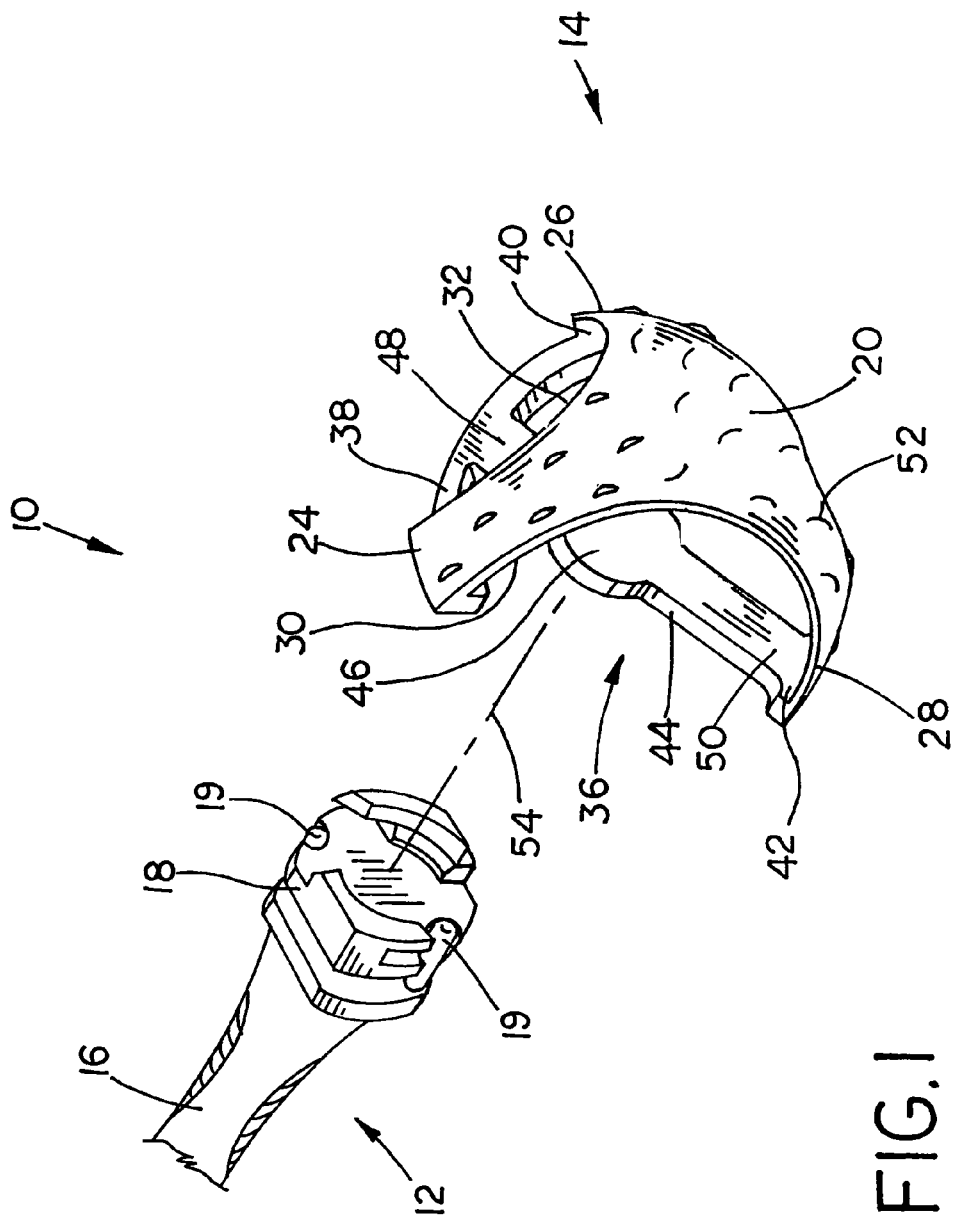

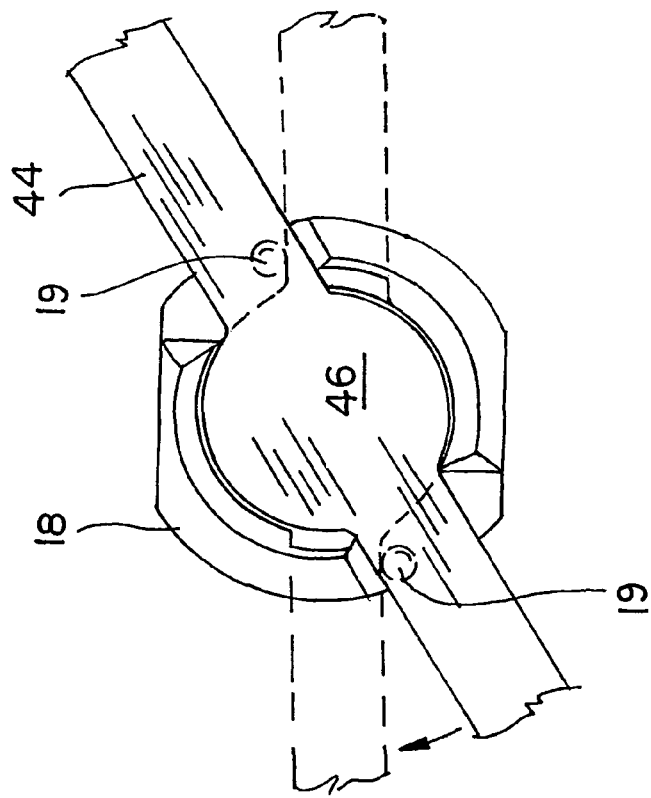
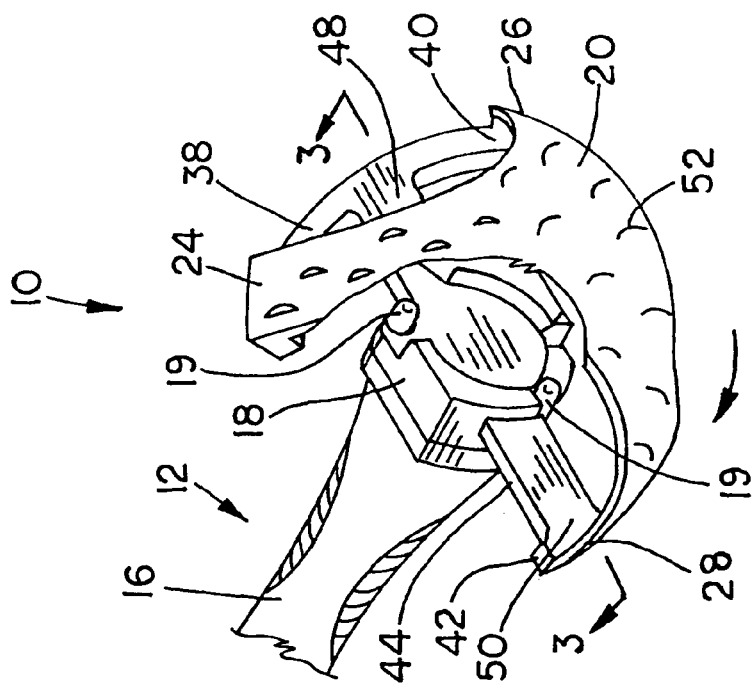

REDUCED PROFILE ORTHOPAEDIC REAMER

BACKGROUND OF THE INVENTION

1. Field of the Invention

The present invention relates to orthopaedic reamers, and, more particularly, to acetabular reamers.

2. Description of the Related Art

Minimally invasive surgical techniques have the advantage of reducing the trauma to tissue surrounding the surgical site during a surgical procedure. The small incision that surgeons are using for minimally invasive hip surgery make it difficult to insert a current full size hemispherical acetabular reamer through the small incision. However, the full size hemispherical acetabular reamer cuts a full hemispherical shape in the acetabulum with minimal wobbling and therefore provides an excellent preparation for the hip joint prosthesis. Additionally, a reamer is required to be connected to a driver, which is in turn connected to a rotational tool. The driver has a specific structure at the proximal (to the surgical site) end thereof, which is compatible with specific attachment mechanisms on the reamers. The drivers represent an investment on the part of the medical institution, and if the reamer is modified to be more compatible with minimally invasive surgical techniques, the driver may be correspondingly modified, which necessitates the purchase of both the driver and the reamer for the medical institution. The purchase of a driver adds cost to the acquisition of the new reamer technology.

Orthopaedic reamers are known that cut off opposing segments of the hemispherical shell of the reamer. The resulting reamer, while having a reduced profile in a certain orientation, is no longer rotationally symmetric. The lack of rotational symmetry can cause vibration and wobbling of the reamer when in use. Such a cut-down reamer design can cut an irregular cavity in the acetabulum, for example, during hip joint prosthesis. An irregular cavity in the acetabulum can reduce the expected lifetime of the hip joint prosthesis, cause discomfort for the patient and increase the wear in the artificial joint, among other problems.

An orthopaedic reamer and driver for minimally invasive surgery are known where the reamer, when attached to the driver, can be rotated from a position where the base of the reamer is approximately parallel to the driver shaft for insertion, to a position where the base of the reamer is approximately perpendicular to the driver shaft for reaming. The reamer is generally a one-piece unit. There are cutouts in the hemispherical shell to allow the reamer to rotate over and clear the driver for a minimal insertion profile. The hemispherical shell includes attachment elements for connecting to the driver where these attachment elements are indentations made in the shell of the reamer. The insertion profile of the reamer is reduced by a pivoting of the reamer, which pivoting is accomplished with a specialized driver.

What is needed in the art is an orthopaedic reamer with a reduced insertion profile, of a reliable design and compatible with an existing driver design, in minimally invasive surgery consistent with the small incision thereof.

SUMMARY OF THE INVENTION

The present invention provides an orthopaedic reamer with a reduced insertion profile of the hemispherical cutting shell by cutting out three portions of the shell and providing a driver attachment connected three base segments of the shell.

The invention comprises, in one form thereof, an orthopaedic reamer, which includes a reamer with a partially hemispherical shell which has a base including three circumferential base segments. The shell has three cutouts each extending to the base. Each of the three circumferential base segments are separated from another of the three circumferential base segments by one of the three cutouts. A driver attachment is directly connected to the three circumferential base segments.

The invention comprises, in another form thereof, an orthopaedic reamer assembly, which includes a driver and a reamer connected to the driver. The reamer includes a partially hemispherical shell having a base including three circumferential base segments. The shell has three cutouts each extending to the base. Each of the three circumferential base segments is separated from another of the three circumferential base segments by one of the three cutouts. A driver attachment is directly connected to the three circumferential base segments, and the driver attachment is connected to the driver.

The invention comprises, in yet another form thereof, an orthopaedic reamer, which includes a reamer with an at least partially hemispherical shell which has a base, and the shell includes a rotational axis. A driver attachment is connected to the base. The driver attachment includes a diametral bar with a first end, a second end, and a centering disk located between the first end and the second end and approximately centered on the rotational axis. The driver attachment further includes a first arm and a second arm directly connected to the first end, and a third arm directly connected to the second end. Each of the first arm, the second arm and the third arm is directly connected to the base.

The invention comprises, in yet another form thereof, a method of connecting an orthopaedic reamer shell to a driver attachment, the method including the steps of: providing a reamer including a partially hemispherical shell having a base including three circumferential base segments, the shell having three cutouts each extending to the base, each of the three circumferential base segments separated from another of the three circumferential base segments by one of the three cutouts; providing a driver attachment including a diametral bar including a first end, a second end and a centering disk located between the first end and the second end and approximately centered on the rotational axis, the driver attachment further including a first arm and a second arm directly connected to the first end, and a third arm directly connected to the second end; and directly connecting each of the first arm, the second arm and the third arm to a respective one of the three circumferential base segments.

An advantage of the present invention is that it provides an orthopaedic reamer with a reduced insertion profile.

Another advantage of the present invention is that it is compatible with an existing driver design.

Yet another advantage of the present invention is that it provides a full hemispherical reaming when cutting.

Yet another advantage of the present invention is that it is a reliable design.

Yet another advantage of the present invention is that it relatively easy and cost effective to manufacture.

Yet another advantage of the present invention is that it is rotationally symmetric with good cutting performance and providing good surgical preparation for a prosthesis.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is an exploded, fragmentary perspective view of an embodiment of an orthopaedic reamer assembly according to the present invention;

FIG. 2 is an assembled, fragmentary perspective view of the orthopaedic reamer assembly of FIG. 1;

FIG. 3 is a cross-sectional view taken along section line 3-3 in FIG. 2, and depicting the driver attachment mechanism seated in the driver (solid lines), and then rotated and locked to the driver (dashed lines);

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 5:
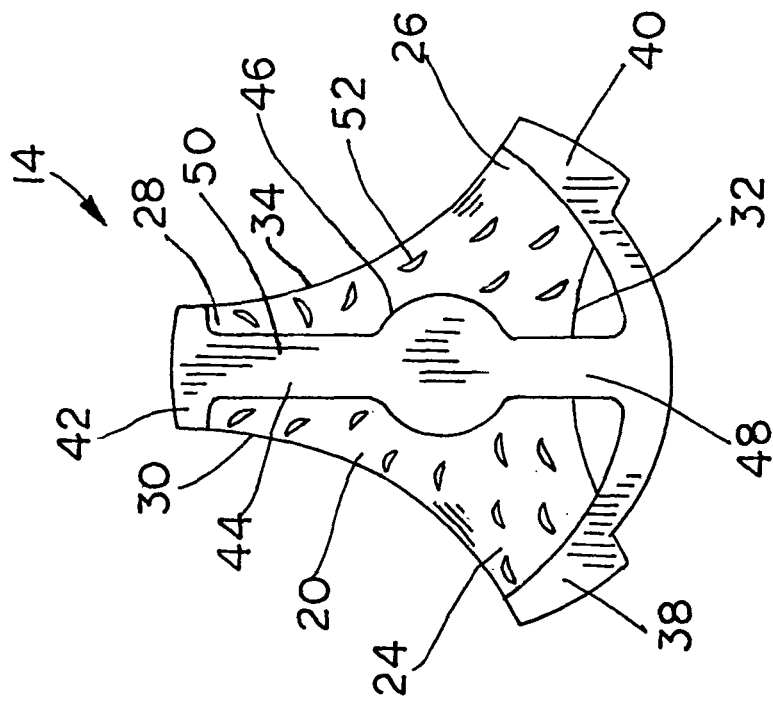
FIG. 5 is a bottom view of the orthopaedic reamer of FIG. 1.

Referring now to the drawings, and more particularly to FIG. 1, there is shown an orthopaedic reamer assembly 10, which includes a driver 12, and a reamer 14 connected to driver 12.

Driver 12 includes a shaft 16 which can be attached to a rotating tool (not shown), and a cutting tool attachment mechanism 18. As shown in FIGS. 2 and 3, locking pins 19 can retract when reamer 14 is initially seated on cutting tool attachment mechanism 18, and then spring back to lock reamer 14 to driver 12.

Figure 4:
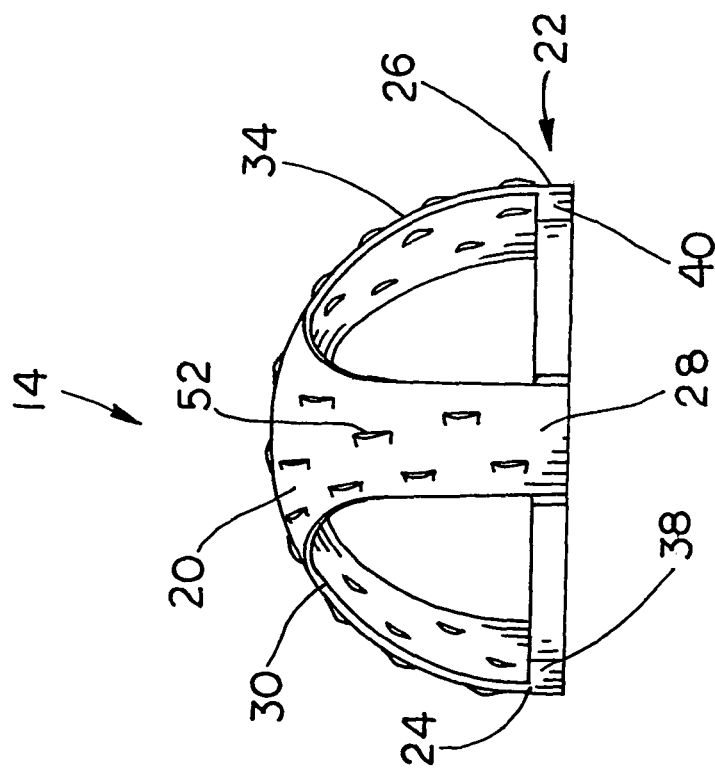
FIG. 4 is a side view of the orthopaedic reamer of FIG. 1.

As shown particularly in FIGS. 4 and 5, reamer 14 includes a partially hemispherical shell 20 which has a base 22 with three circumferential base segments 24, 26, 28. Shell 20 has three cutouts 30, 32, 34, where each cutout extends to base 22, and wherein each cutout represents an absence of material relative to a full hemispherical shell. Each of circumferential base segments 24, 26, 28 are separated from another of the three circumferential base segments 24, 26, 28 by one of the three cutouts 30, 32, 34. A driver attachment 36 is directly connected to circumferential base segments 24, 26, 28. Driver attachment 36 is also connected to driver 12 when reamer 14 is connected to driver 12. The center of each cutout 30, 32, 34 can be separated by approximately 120° from the center of another cutout, although other separations between 0° and 360° are possible. Similarly, the center of each circumferential base segments 24, 26, 28 can be separated by approximately 120° from the center of another circumferential base segment, although other separations between 0° and 360° are possible.

Driver attachment 36 includes a first arm 38, a second arm 40 and a third arm 42, and each of arms 38, 40 and 42 are directly connected to a respective one of circumferential base segments 24, 26, 28. Driver attachment 36 can include a diametral bar 44 with a centering disk 46 therein, and further includes a first end 48 and a second end 50. First arm 38 and second arm 40 are directly connected to first end 48, and third arm 42 is directly connected to second end 50.

Diametral bar 44, first arm 38, second arm 40 and third arm 42 can comprise a kedge anchor-shape as shown particularly in FIG. 6. The reamer can be an acetabular reamer 14, and shell 20 can include a plurality of cutting surfaces or teeth 52. Shell 20 can include a rotational axis 54, and centering disk 46 can be located between first end 48 and second end 50 and approximately centered on rotational axis 54.

In use, the present invention discloses a method of connecting an orthopaedic reamer shell 20 to a driver attachment 36, the method including the steps of: providing a reamer 14 including a partially hemispherical shell 20 having a base 22 including three circumferential base segments 24, 26, 28, shell 20 having three cutouts 30, 32, 34 each extending to base 22, each of circumferential base segments 24, 26, 28 separated from another of circumferential base segments 24, 26, 28 by one of the three cutouts 30, 32, 34; providing a driver attachment 36 including a diametral bar 44 having a first end 48, a second end 50 and a centering disk 46 located between first end 48 and second end 50 and approximately centered on rotational axis 54, where driver attachment 36 further includes a first arm 38 and a second arm 40 directly connected to first end 48, and a third arm 42 directly connected to second end 50; and directly connecting each of arms 38, 40, 42 to a respective one of circumferential base segments 24, 26, 28.

The method of the present invention can further include the step of shaping driver attachment 36 approximately in a form of a kedge anchor; and the step of forming a plurality of cutting surfaces 52 in shell 20.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic reamer, comprising:
   a reamer including a fixed at least partially hemispherical shell including a rotational axis having an active cutting surface and having a base, said shell having three cutouts each extending to said base and significantly interrupting said cutting surface to form a discontinuous rim defining three active cutting surfaces and reduce the profile of said reamer, as viewed in a direction parallel to said rotational axis wherein said three active cutting surfaces are substantially identical to and fixed relative to one another;
   a driver attachment connected to said base, said driver attachment including a diametral bar including a first end, a second end and a centering disk located between said first end and said second end and approximately centered on said rotational axis, said driver attachment further including a first arm and a second arm directly connected to said first end, and a third arm directly connected to said second end, each of said first arm, said second arm and said third arm directly connected to said base,
   wherein said diametral bar, said first arm, said second arm and said arm comprise a kedge anchor-shape.

2. The orthopaedic reamer of claim 1, wherein each of said first arm and said second arm include an arc-shape.

3. The orthopaedic reamer of claim 1, wherein said reamer is an acetabular reamer, said shell includes a plurality of cutting surfaces.

* * * * *